United States Patent [19]
Tam

[11] Patent Number: 5,880,094
[45] Date of Patent: Mar. 9, 1999

[54] POLYPEPTIDES THAT STIMULATE BONE GROWTH

[75] Inventor: Cherk Shing Tam, Oakville, Canada

[73] Assignee: Osteopharm Limited, Mississauga, Canada

[21] Appl. No.: 487,074

[22] Filed: Jun. 7, 1995

[51] Int. Cl.[6] .......................... A61K 38/04; A61K 38/00; C07K 7/08; C07K 14/51

[52] U.S. Cl. ................................ 514/12; 514/13; 514/14; 530/300; 530/324; 530/326

[58] Field of Search ...................... 530/300, 350, 530/324, 326; 514/2–14

[56] References Cited

U.S. PATENT DOCUMENTS

| | | | |
|---|---|---|---|
| 5,461,034 | 10/1995 | Rodan et al. | 514/14 |
| 5,578,569 | 11/1996 | Tam | 514/12 |

FOREIGN PATENT DOCUMENTS

| | | |
|---|---|---|
| 2231872 | 6/1990 | United Kingdom . |
| WO9006321 | 6/1990 | WIPO . |
| WO9528172 | 10/1995 | WIPO . |

OTHER PUBLICATIONS

Castor et al. (1992) Arthritis and Rheumatism 35:782–93.
Walz and Baggiolini (1990) J. Exp. Med. 171:449–54.
Begg et al. (1978) Biochemistry 17:1739–44.
Castor et al. (1983) Proc. Natl. Acad. Sci. USA 80:765–69.
Castor et al. (1989) Biochem. Biophys. Res. Commun. 163:1071–78.

*Primary Examiner*—W. Gary Jones
*Assistant Examiner*—Debra Shoemaker
*Attorney, Agent, or Firm*—Foley & Lardner

[57] ABSTRACT

Polypeptides which stimulate bone growth are described based on the sequences: (a) Gly Ile Gly Lys Arg Thr Asn Glu His Thr Ala Asp Cys Lys Ile Lys Pro Asn Thr Leu His Lys Lys Ala Ala Glu Thr Leu Met Val; (b) Gly Ile Gly Lys Arg Thr Asn Glu His Thr Ala Asp Cys Lys Ile Lys Pro Asn Thr Leu His Lys Lys Ala Ala; (c) Gly Ile Gly Lys Arg Thr Asn Glu His Thr Ala Asp Cys Lys Ile Lys Pro Asn Thr Leu; and (d) Gly Ile Gly Lys Arg Thr Asn Glu His Thr Ala Asp Cys Lys Ile. The associated nucleotide sequences, methods of preparation and use, and antibodies and kits based upon them are described, as well.

40 Claims, 6 Drawing Sheets

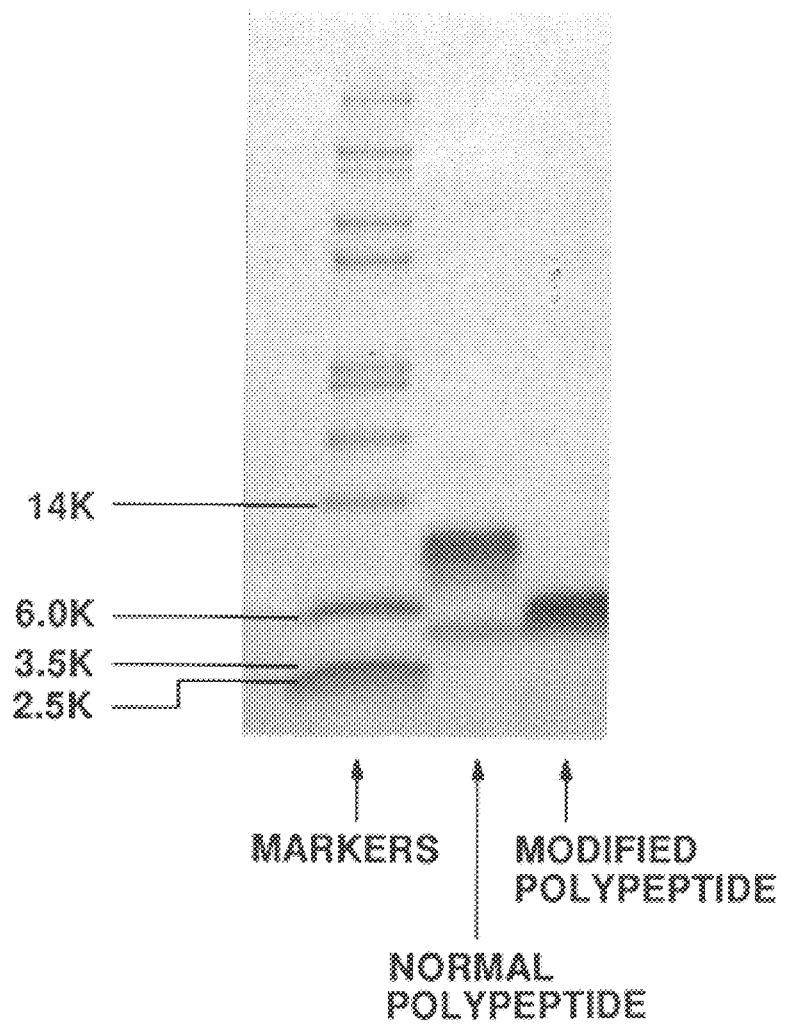

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Gly  Ile  Gly  Lys  Arg  Thr  Asn  Glu  His  Thr  Ala  Asp  Cys  Lys  Ile  Lys
1                   5                        10                            15

Pro  Asn  Thr  Leu  His  Lys  Lys  Ala  Ala  Glu  Thr  Leu  Met  Val  Leu  Asp
               20                       25                       30

Gln  Asn  Gln  Pro
               35
```

( 2 ) INFORMATION FOR SEQ ID NO:2:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: linear ( i x ) FEATURE:
        ( A ) NAME/KEY: Modified-site
        ( B ) LOCATION: 1
        ( D ) OTHER INFORMATION: /note= "Xaa is N-acetyl glycine"

( x i ) SEQUENCE DESCRIPTION: SEQ ID NO:2:

```
Xaa  Ile  Gly  Lys  Arg  Thr  Asn  Glu  His  Thr  Ala  Asp  Cys  Lys  Ile  Lys
1                   5                        10                            15

Pro  Asn  Thr  Leu  His  Lys  Lys  Ala  Ala  Glu  Thr  Leu  Met  Val  Leu  Asp
               20                       25                       30

Gln  Asn  Gln  Pro
               35
```

( 2 ) INFORMATION FOR SEQ ID NO:3:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

```
Gly  Ile  Gly  Lys  Arg  Thr  Asn  Glu  His  Thr  Ala  Asp  Ala  Lys  Ile  Lys
1                   5                        10                            15

Pro  Asn  Thr  Leu  His  Lys  Lys  Ala  Ala  Glu  Thr  Leu  Met  Val  Leu  Asp
               20                       25                       30

Gln  Asn  Gln  Pro
               35
```

( 2 ) INFORMATION FOR SEQ ID NO:4:

( i ) SEQUENCE CHARACTERISTICS:
        ( A ) LENGTH: 30 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

Gly Ile Gly Lys Arg Thr Asn Glu His Thr Ala Asp Cys Lys Ile Lys
1               5                   10                  15

Pro Asn Thr Leu His Lys Lys Ala Ala Glu Thr Leu Met Val
            20                  25                  30

( 2 ) INFORMATION FOR SEQ ID NO:5:

( i ) SEQUENCE CHARACTERISTICS:
( A ) LENGTH: 25 amino acids
( B ) TYPE: amino acid
( C ) STRANDEDNESS:
( D ) TOPOLOGY: linear ( x i ) SEQUENCE DESCRIPTION: SEQ ID NO:5:

Gly Ile Gly Lys Arg Thr Asn Glu His Thr Ala Asp Cys Lys Ile Lys
1               5                   10                  15

Pro Asn Thr Leu His Lys Lys Ala Ala
            20                  25

( 2 ) INFORMATION FOR SEQ ID NO:6:

( i ) SEQUENCE CHARACTERISTICS:
( A ) LENGTH: 20 amino acids
( B ) TYPE: amino acid
( C ) STRANDEDNESS:
( D ) TOPOLOGY: linear ( x i ) SEQUENCE DESCRIPTION: SEQ ID NO:6:

Gly Ile Gly Lys Arg Thr Asn Glu His Thr Ala Asp Cys Lys Ile Lys
1               5                   10                  15

Pro Asn Thr Leu
            20

( 2 ) INFORMATION FOR SEQ ID NO:7:

( i ) SEQUENCE CHARACTERISTICS:
( A ) LENGTH: 15 amino acids
( B ) TYPE: amino acid
( C ) STRANDEDNESS:
( D ) TOPOLOGY: linear ( x i ) SEQUENCE DESCRIPTION: SEQ ID NO:7:

Gly Ile Gly Lys Arg Thr Asn Glu His Thr Ala Asp Cys Lys Ile
1               5                   10                  15

( 2 ) INFORMATION FOR SEQ ID NO:8:

( i ) SEQUENCE CHARACTERISTICS:
( A ) LENGTH: 16 amino acids
( B ) TYPE: amino acid
( C ) STRANDEDNESS:
( D ) TOPOLOGY: linear ( x i ) SEQUENCE DESCRIPTION: SEQ ID NO:8:

Leu His Lys Lys Ala Ala Glu Thr Leu Met Val Leu Asp Gln Asn Gln
1               5                   10                  15

( 2 ) INFORMATION FOR SEQ ID NO:9:

( i ) SEQUENCE CHARACTERISTICS:
( A ) LENGTH: 15 amino acids
( B ) TYPE: amino acid
( C ) STRANDEDNESS:
( D ) TOPOLOGY: linear ( x i ) SEQUENCE DESCRIPTION: SEQ ID NO:9:

Leu His Lys Lys Ala Ala Glu Thr Leu Met Val Leu Asp Gln Asn
1               5                   10                  15

( 2 ) INFORMATION FOR SEQ ID NO:10:

( i ) SEQUENCE CHARACTERISTICS:
      ( A ) LENGTH: 14 amino acids
      ( B ) TYPE: amino acid
      ( C ) STRANDEDNESS:
      ( D ) TOPOLOGY: linear ( x i ) SEQUENCE DESCRIPTION: SEQ ID NO:10:

Leu His Lys Lys Ala Ala Glu Thr Leu Met Val Leu Asp Gln
1               5                   10

( 2 ) INFORMATION FOR SEQ ID NO:11:

( i ) SEQUENCE CHARACTERISTICS:
      ( A ) LENGTH: 13 amino acids
      ( B ) TYPE: amino acid
      ( C ) STRANDEDNESS:
      ( D ) TOPOLOGY: linear ( x i ) SEQUENCE DESCRIPTION: SEQ ID NO:11:

Leu His Lys Lys Ala Ala Glu Thr Leu Met Val Leu Asp
1               5                   10

( 2 ) INFORMATION FOR SEQ ID NO:12:

( i ) SEQUENCE CHARACTERISTICS:
      ( A ) LENGTH: 23 amino acids
      ( B ) TYPE: amino acid
      ( C ) STRANDEDNESS:
      ( D ) TOPOLOGY: linear ( x i ) SEQUENCE DESCRIPTION: SEQ ID NO:12:

Thr Ala Asp Cys Lys Ile Lys Pro Asn Thr Leu His Lys Lys Ala Ala
1               5                   10                  15

Glu Thr Leu Met Val Leu Asp
                20

( 2 ) INFORMATION FOR SEQ ID NO:13:

( i ) SEQUENCE CHARACTERISTICS:
      ( A ) LENGTH: 30 amino acids
      ( B ) TYPE: amino acid
      ( C ) STRANDEDNESS:
      ( D ) TOPOLOGY: linear ( x i ) SEQUENCE DESCRIPTION: SEQ ID NO:13:

Arg Thr Asn Glu His Thr Ala Asp Cys Lys Ile Lys Pro Asn Thr Leu
1               5                   10                  15

His Lys Lys Ala Ala Glu Thr Leu Met Val Leu Asp Gln Asn
                20                  25                  30

( 2 ) INFORMATION FOR SEQ ID NO:14:

( i ) SEQUENCE CHARACTERISTICS:
      ( A ) LENGTH: 11 amino acids
      ( B ) TYPE: amino acid
      ( C ) STRANDEDNESS:
      ( D ) TOPOLOGY: linear ( x i ) SEQUENCE DESCRIPTION: SEQ ID NO:14:

Arg Thr Asn Glu His Thr Ala Asp Cys Lys Ile
1               5                   10

(2) INFORMATION FOR SEQ ID NO:15:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO:15:

```
GGGATCGGAA AACGAACAAA TGAACATACG GCAGATTGTA AAATTAAACC GAACACCTTG        60
CATAAAAAAG CTGCAGAGAC TTTAATGGTC                                         90
```

(2) INFORMATION FOR SEQ ID NO:16:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:16:

```
GGGATCGGAA AACGAACAAA TGAACATACG GCAGATTGTA AAATTAAACC GAACACCTTG        60
CATAAAAAAG CTGCA                                                         75
```

(2) INFORMATION FOR SEQ ID NO:17:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:17:

```
GGGATCGGAA AACGAACAAA TGAACATACG GCAGATTGTA AAATTAAACC GAACACCTTG        60
```

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:18:

```
GGGATCGGAA AACGAACAAA TGAACATACG GCAGATTGTA AAATT                        45
```

POLYPEPTIDES THAT STIMULATE BONE GROWTH

The present invention relates to polypeptides which stimulate bone growth.

Understanding of issues related to bone growth and strength has progressed over the years, a summary being provided in international patent application No. PCT/CA 94/00144, published under international publication No. WO 94/20615 on Sep. 15, 1994, the contents of which application are incorporated herein by reference.

Various approaches to treatment of diseases involving reduction of bone mass and accompanying disorders are exemplified in the patent literature. For example, international patent application published Sep. 17, 1992 under No. 92/15615 describes a protein derived from a porcine pancreas which acts to depress serum calcium levels for treatment of bone disorders that cause elevation of serum calcium levels. European Patent Application No. 504 938 published Sep. 23, 1992 describes the use of di- or tripeptides which inhibit cysteine protease in the treatment of bone diseases. International patent application published Sep. 3, 1992 under No. 92/14481 discloses a composition for inducing bone growth, the composition containing activin and bone morphogenic protein. European Patent Application No. 499 242 published Aug. 19, 1992 describes the use of cell growth factor compositions thought to be useful in bone diseases involving bone mass reduction because they cause osteoblast proliferation. International patent application published Jun. 25, 1992 under No. 92/10515 1992 describes a drug containing the human N-terminal parathyroid hormone (PTH) fragment 1–37. European Patent Application No. 451 867 published Sep. 16, 1991 describes parathyroid hormone peptide antagonists for treating dysbolism associated with calcium or phosphoric acid, such as osteoporosis.

A relatively short half life of PTH in the blood serum and the positive effect of intermittent PTH injection on bone volume led the present investigator to the hypothesis that PTH may in some way lead to induction of a second factor into the circulatory system. The presence of such a second factor in blood serum of rats and of humans has thus been investigated.

It has been found possible to isolate from rat blood serum a polypeptide substance which, upon administration to rats incapable of producing PTH (parathyroidectomized rats), produces an increase in the observed bone mineral apposition rate. A nucleic acid probe, based on the amino acid sequence of the rat peptide was synthesized and used to screen a human liver cDNA fetal library in order to isolate a human nucleic acid sequence coding for a human bone apposition polypeptide. A polypeptide derived from the nucleic acid sequence was thus chemically synthesized according to the derived sequence Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro (SEQ ID NO:1). It has been observed that the bone apposition rate in intact rats increases in a dose dependent fashion upon administration of this chemically synthesized compound. Reduced bone growth, normally observed for ovariectomized rats, was observed not to occur in rats after being administered with the polypeptide over a four week period beginning two weeks after ovariectomization. Bone calcium density was found to be maintained in ovariectomized rats administered with the polypeptide over an eight week period beginning eight weeks after ovariectomization.

It is thought possible that the active polypeptide is a dimer of the foregoing sequence, there being evidence of significant dimer formation, presumably due to a disulfide bridge between two polypeptides having the sequence shown.

Accordingly, the present invention includes dimeric polypeptides in which each monomer comprises one of the amino acid sequences of SEQ ID NOS: 4, 5, 6, or 7, and the monomers are linked to each other by a disulfide bridge between the cysteine residues of the respective sequences. These dimeric polypeptides may include the entirety or just a part of the amino acid sequences of SEQ ID NOS: 4, 5, 6, or 7, as well as analogs thereof in which the amino acids are substituted, deleted, or added provided that the bone stimulatory activity in mammals derived from the three dimensional conformation of the sequence is preserved. Conjugates and analogs of the polypeptide dimers may also be formed.

A modified form of the polypeptide containing a cys→ala substitution was thus synthesized: Gly Ile Gly Lys Arg Thr Asn Glu His Thr Ala Asp Ala Lys Ile Lys Pro Asn Thr Leu His Lys Lys Ala Ala Glu Thr Leu Met Val Leu Asp Gln Asn Gln Pro (SEQ ID NO:3). Some of the bone stimulatory effects of the "normal" polypeptide (SEQ ID NO:1) were found for the modified polypeptide.

In other experiments, the bone mineral apposition rate in rats administered with rabbit anitbodies to the normal polypeptide (SEQ ID NO:1) was found to be suppressed. The suppression was found to be attenuated in rats administered with both the normal polypeptide and antibodies to same.

Further, N-terminus polypeptide fragments of the normal polypeptide (SEQ ID NO:1) have now been synthesized and each has been found to have bone stimulatory effects:

SEQ ID NO:4:
Gly Ile Gly Lys Arg Thr Asn Glu His Thr Ala Asp Cys Lys Ile Lys Pro Asn Thr Leu His Lys Lys Ala Ala Glu Thr Leu Met Val

SEQ ID NO:5:
Gly Ile Gly Lys Arg Thr Asn Glu His Thr Ala Asp Cys Lys Ile Lys Pro Asn Thr Leu His Lys Lys Ala Ala

SEQ ID NO:6:
Gly Ile Gly Lys Arg Thr Asn Glu His Thr Ala Asp Cys Lys Ile Lys Pro Asn Thr Leu

SEQ ID NO:7:
Gly Ile Gly Lys Arg Thr Asn Glu His Thr Ala Asp Cys Lys Ile

Other non-N-terminus polypeptide fragments of the normal polypeptide (SEQ ID NO:1) have also been synthesized and have been found to lack the bone stimulatory effect found for the normal polypeptide:

SEQ ID NO:8:
Leu His Lys Lys Ala Ala Glu Thr Leu Met Val Leu Asp Gln Asn Gln

SEQ ID NO:9:
Leu His Lys Lys Ala Ala Glu Thr Leu Met Val Leu Asp Gln Asn

SEQ ID NO:10:
Leu His Lys Lys Ala Ala Glu Thr Leu Met Val Leu Asp Gln

SEQ ID NO:11:
Leu His Lys Lys Ala Ala Glu Thr Leu Met Val Leu Asp

SEQ ID NO:12:
Thr Ala Asp Cys Lys Ile Lys Pro Asn Thr Leu His Lys Lys Ala Ala Glu Thr Leu Met Val Leu Asp

SEQ ID NO:13:
Arg Thr Asn Glu His Thr Ala Asp Cys Lys Ile Lys Pro Asn Thr Leu His Lys Lys Ala Ala Glu Thr Leu Met Val Leu Asp Gln Asn

SEQ ID NO:14:
Arg Thr Asn Glu His Thr Ala Asp Cys Lys Ile

BRIEF DESCRIPTION OF THE DRAWINGS

In the following description, reference is made to accompanying drawings, wherein, FIG. 1 graphically depicts the bone mineral apposition rate ($\mu$m per day) in rats provided with the chemically synthesized human N-acetyl (N-terminus) polypeptide (SEQ ID NO:2) through implantation in parathyroidectomized rats. The error bars indicate ±1 standard deviation (S.D.). The value of p was less than 0.001.

FIG. 6 shows a tricine SDS electrophoretic gel of the human chemically synthesized polypeptide (SEQ ID NO:1) and the same polypeptide containing a cys→ala substitution (SEQ ID NO:3).

METHODOLOGY

The applicable methodology as described in the General Methodology section of international patent application No. PCT/CA 94/00144 was followed here.

Toxicity Experiments Involving N-Terminal Acetyl Chemically Synthesized Polypeptide (SEQ ID NO:2)

A miniosmotic pump (Alzet) was loaded with about 1.5 ml of the chemically synthesized peptide having an N-terminal acetyl group (SEQ ID NO:2) in 0.1% acetic acid so as to give a calculated daily delivery of about 25 $\mu$g per day. A pump was implanted under the subcutaneous fascia of the dorsal aspect of the left side of the thorax of five rats which had been parathyroidectomized seven days earlier. Five similarly parathyroidectomized rats received similar implants containing only 0.1% acetic acid. Five intact rats were also used as controls.

Twenty-eight days later 0.5 ml of an aqueous solution of tetracycline hydrochloride was injected intramuscularly into the right gluteus maximus of each of the implanted rats, as described previously. Another 48 hours later, a second injection of tetracycline hydrochloride solution was injected. The rats were sacrificed another 24 hours later.

Figure 1:
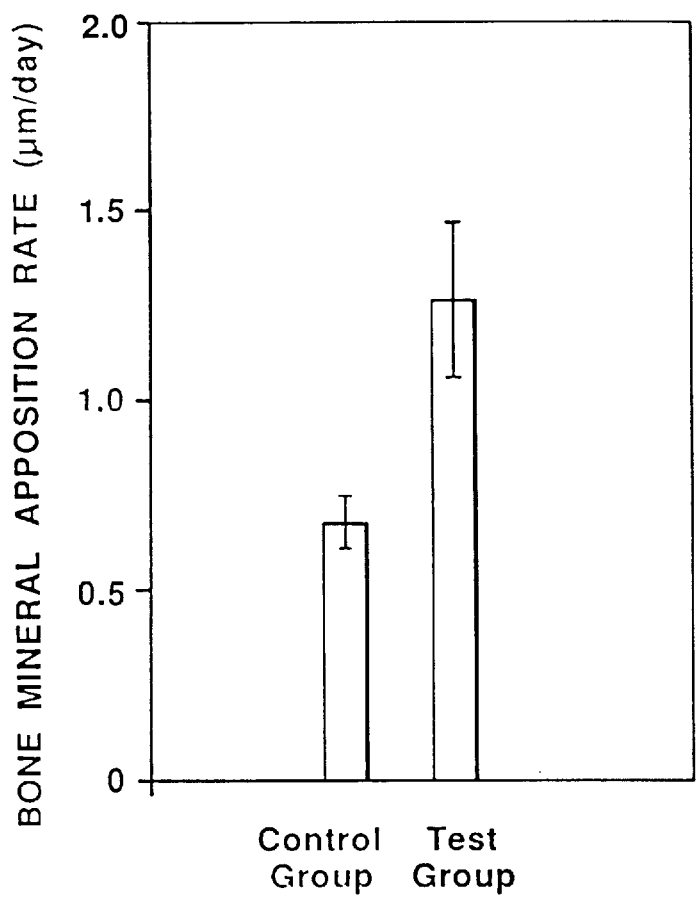

The bone mineral apposition rate was determined by examination of a cross-section of the lower metaphysis of the right femur of each of the ten rats which had been given implants. The results are summarized in Table One depicted graphically in FIG. 1.

TABLE ONE

Comparison of the Group Arithmetic Means Among Groups

|  | Test Group | Control Group |
| --- | --- | --- |
| Mean | 1.27 $\mu$m/d | 0.67 $\mu$m/d |
| S.D. | 0.18 $\mu$m/d | 0.08 $\mu$m/d |
| N | 5 | 5 |
|  | t | d.f |
| Test Group vs Control Group | 7.14 | 8 |

Histological evaluation of selected tissues of the five rats of each of the groups indicated in Table One were carried out microscopically. No evidence of toxic lesions was found. Experiments Involving Ovariectomized Rats and the Normal Chemically Synthesized Polypeptide, Administration Over a Four Week Period Ovariectomies were performed on six female Sprague-Dawley rats, each sedated with 1 mg of sodium barbiturate I.P. Sham operations were carried out a second group of six rats. The rats were given two weeks to recover from the operations.

The six ovariectomized rats were injected subcutaneously with 100 $\mu$l of a 0.1% acetic acid solution containing 100 $\mu$g of the chemically synthesized peptide (SEQ ID NO:1) every 24 hours for 28 days. On day 25, a tetracycline hydrochloride solution was injected intramuscularly into each rat so as to give 24 mg per Kg of body weight, as described previously. On day 27, a second dose of tetracycline hydrochloride was injected and the rats were sacrificed on the 28th day.

A second group of six ovariectomized rats, was similarly treated with a 0.1% acetic acid solution containing no peptide over the same 28 day period. A third group of six rats, each of which had undergone the sham operation, was similarly treated with a 0.1% acetic acid solution containing no peptide over the same 28 day period. A fourth group of six intact rats was similarly treated with a 0.1% acetic acid solution containing no peptide over the same 28 day period.

Postmortem blood was taken by cardiac puncture and serum frozen until analyzed. A full autopsy was performed on each rat. No ill effects were observed in the rats treated with the polypeptide.

Each of the right femurs was dissected out from its soft tissue, fixed for two days, and X-rays taken at 70 kV for 1 min., 2 min., and 3 min. The 3 minute exposures gave the most satisfactory results. The bone densities of the femurs from the second group of rats, the ovariectomized rats not treated with the peptide, showed a visibly lower bone density.

The right femur of each rat was decalcified separately. The decalcification fluid consisted of 10% formic acid (v/v) and 5% sodium citrate (w/v) at pH 3.0. Each bone was placed in 6 ml of the decalcification fluid. The fluid was replaced after 4 days, again after another 4 days, again after another 2 days, and again after another 3 days. After another 2 days, the decalcification fluid was removed and replaced by deionized water, and the sample agitated for 2 days. The water changed after two days and again after another day. After another day, all of the fluid samples for each rat were combined and the final volume of each adjusted to 50 ml with deionized water.

Figure 2:
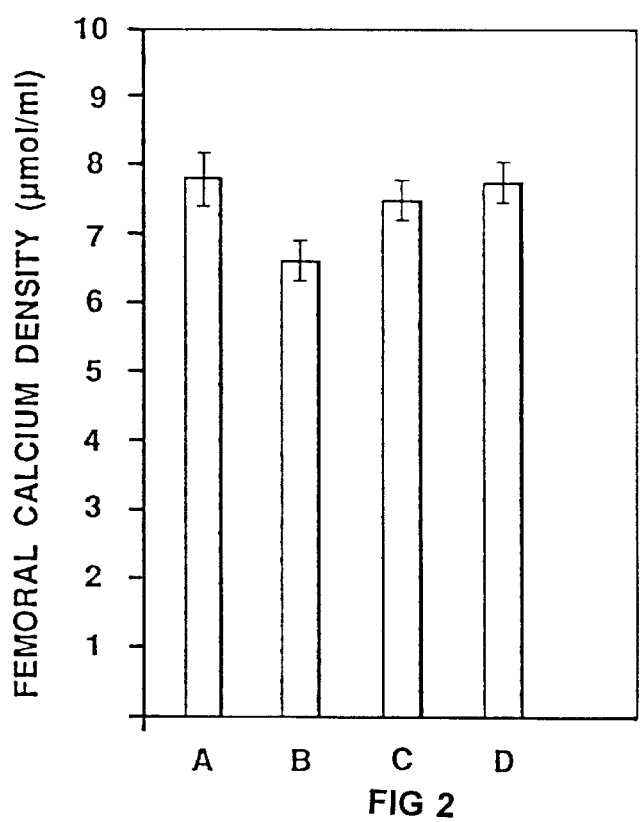
FIG. 2 graphically depicts right femoral bone calcium density of rats treated over a four week period. Group A rats were ovariectomized and injected daily with the chemically synthesized normal peptide (SEQ ID NO:1). Group B rats were ovariectomized and injected daily with control solution. Group C rats were subject to sham ovariectomization operations and injected daily with control solution. Group D were intact rats injected daily with control solution. The error bars indicate ±1 standard deviation (S.D.).

The volume of each right femur was determined by determining the volume of water displaced when the bone was immersed in water. The calcium concentration of each sample was determined according to standard methods and the calcium density of each bone calculated. The results are tabulated in Table Two and graphically depicted in FIG. 2. As can be seen, the bone calcium concentration measured for the ovariectomized rats treated with the peptide (SEQ ID NO:1) appears to be normal, while the calcium concentration of the untreated ovariectomized rats is depressed.

TABLE TWO

Right Femoral Calcium Concentration of Ovariectomized Rats

|  | Group A | Group B | Group C | Group D |
|---|---|---|---|---|
| Mean ($\mu$mol/ml) | 7.57 | 6.61 | 7.45 | 7.69 |
| N | 6 | 6 | 6 | 6 |
| S.D. | 0.38 | 0.29 | 0.28 | 0.31 |

| GROUP | t | d.f. | p |
|---|---|---|---|
| A vs B | 4.90 | 10 | <0.001 |
| A vs C | 0.62 | 10 | >0.5 |
| A vs D | 0.60 | 10 | >0.5 |
| B vs C | 5.08 | 10 | <0.001 |
| B vs D | 6.20 | 10 | <0.001 |
| C vs D | 1.40 | 10 | >0.1 |

Figure 3:
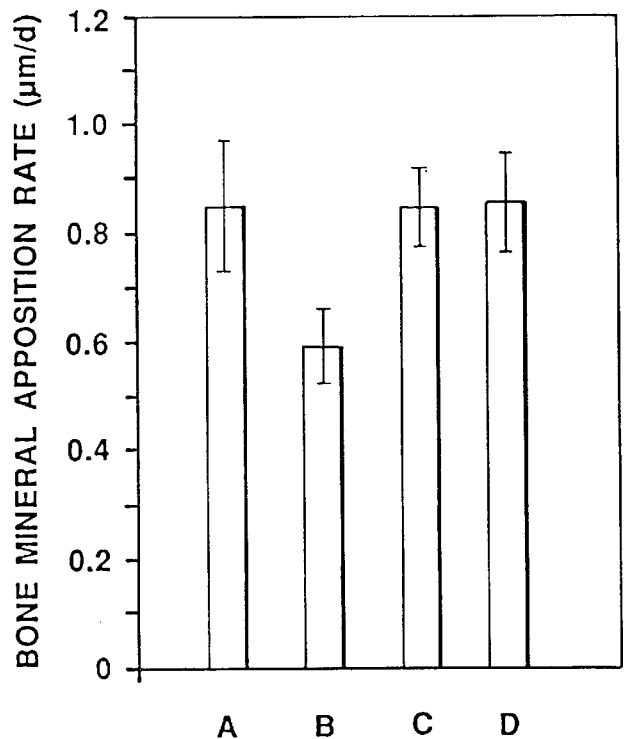
FIG. 3 graphically depicts the bone mineral apposition rate of rats as determined by tetracycline labelling after treatment as described in connection with FIG. 2. The error bars indicate ±1 standard deviation (S.D.).

The bone mineral apposition rate was determined, as described previously, by measurement of the lower metaphysis of the left femur. The results are tabulated in Table Three and graphically depicted in FIG. 3.

TABLE THREE

Bone Mineral Apposition Rates of Ovariectomized Rats

|  | Group A | Group B | Group C | Group D |
|---|---|---|---|---|
| Mean ($\mu$m/day) | 0.90 | 0.59 | 0.85 | 0.86 |
| N | 6 | 6 | 6 | 6 |
| S.D. | 0.12 | 0.07 | 0.07 | 0.09 |

| GROUP | t | d.f. | p |
|---|---|---|---|
| A vs B | 5.39 | 10 | <0.001 |
| A vs C | 0.87 | 10 | >0.5 |
| A vs D | 0.21 | 10 | >0.5 |
| B vs C | 6.29 | 10 | <0.001 |
| B vs D | 5.93 | 10 | <0.001 |
| C vs D | 0.21 | 10 | >0.5 |

Experiments Involving Ovariectomized Rats and the Normal Chemically Synthesized Polypeptide, Administration Over an Eight Week Period Eight weeks after ovariectomization, five ovariectomized rats were injected subcutaneously with 100 $\mu$l of a 0.1% acetic acid solution containing 100 $\mu$g of the chemically synthesized peptide in which the N-terminal amino group was modified with an acetyl group (SEQ ID NO:2). This was done every 24 hours for eight weeks. On day 54, a tetracycline hydrochloride solution was injected intramuscularly into the right gluteus maximus of each rat so as to give 24 mg per Kg of body weight, as described previously. On day 56, a second dose of tetracycline hydrochloride was injected and the rats were sacrificed on the 57th day.

A second group of seven ovariectomized rats, was similarly treated with a 0.1% acetic acid solution containing no peptide over the same period. A third group of five rats, each of which had undergone the sham operation, was similarly treated with a 0.1% acetic acid solution containing no peptide over the same period. A fourth group of five intact rats was similarly treated with a 0.1% acetic acid solution containing no peptide over the same 8 week period. Two rats of the second group became ill during the 8 week period and were sacrificed prematurely.

Postmortem blood was taken by cardiac puncture and serum frozen until analyzed. An autopsy was performed on each rat. No obvious pathology was observed in the rats except for surgical scars and atrophy of the uterus and vagina of ovariectomized rats.

Figure 4:
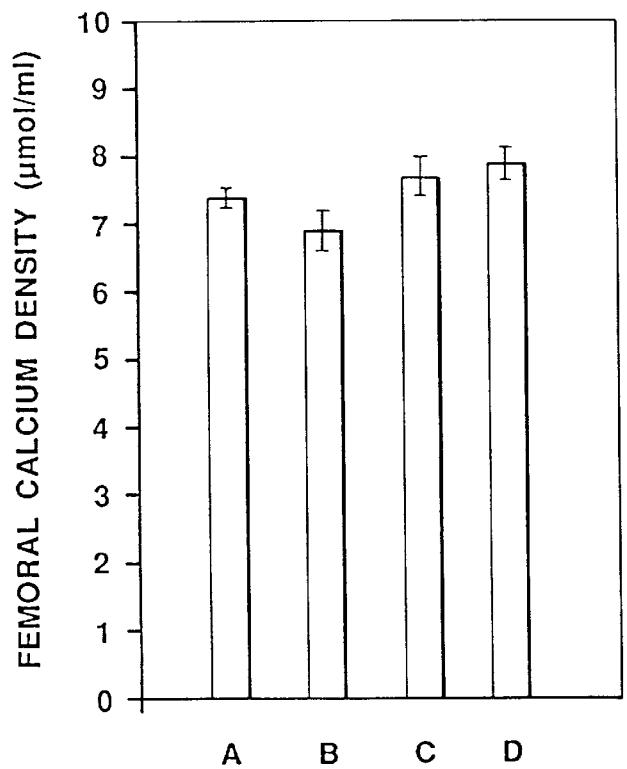
FIG. 4 graphically depicts femoral bone calcium concentration of rats treated over an eight week period. Group A' rats were ovariectomized and injected daily with the chemically synthesized normal peptide (SEQ ID NO:1) beginning eight weeks after the operation. Group B rats were similarly ovariectomized and injected daily with control solution. Group C rats were subject to sham ovariectomization operations and injected daily with control solution. Group D were intact rats injected daily with control solution. The error bars indicate ±1 standard deviation (S.D.).

The right femurs were decalcified and calcium density determined as before. The results are presented in Table Four and FIG. 4.

TABLE FOUR

Right Femoral Calcium Concentration of Ovariectomized Rats

|  | Group A | Group B | Group C | Group D |
|---|---|---|---|---|
| Mean ($\mu$mol/ml) | 7.37 | 6.89 | 7.69 | 7.87 |
| N | 5 | 5 | 5 | 5 |
| S.D. | 0.15 | 0.32 | 0.30 | 0.24 |

| GROUP | t | d.f. | p |
|---|---|---|---|
| A vs B | 3.85 | 6 | <0.005 |
| A vs C | 1.17 | 6 | >0.2 |
| A vs D | 3.01 | 6 | <0.01 |
| B vs C | 4.03 | 6 | <0.005 |
| B vs D | 5.41 | 6 | <0.001 |
| C vs D | 1.60 | 6 | >0.1 |

Synthesis of Antibodies to Chemically Synthesized Protein (SEQ ID NO:1)

The chemically synthesized protein (SEQ ID NO:1) was coupled to KLH (keyhole limpet hemacyanin) with three different cross-linkers, as described below.

GLUTARALDEHYDE COUPLING

In 2.5 ml of a PBS solution made up of 2.7 mM KCl, 1.2 mM $KH_2PO_4$, 138 mM NaCl, 8.1 mM $Na_2HPO_4$, were diluted 5 mg of the peptide (SEQ ID NO:1) o obtain a final peptide concentration of 2 mg/ml. 10 mg of KLH were diluted in 5.0 ml PBS to obtain a final concentration of 2 mg/ml. To 1.25 ml of the KLH solution were added 1.25 ml of the peptide solution. Glutaraldehyde was added to a final concentration of 0.25%. The resultant solution was stirred for 1 hour at room temperature. After stirring, the solution was dialysed against 1 liter of PBS. The PBS was changed three times.

Carbodiimide (EDC) Coupling

Peptide and KLH solutions were prepared as described in the preceding section. To 1.25 ml KLH solution were added 1.25 ml peptide solution. To the resultant solution were added 2.5 mg of EDC. The solution was stirred constantly at room temperature for 4 hours and then dialysed against 1 liter of PBS. The PBS was changed three times.

M-MALEIMIDOBENZOYL-N-HYDROXYSUCCINIMIDE ESTER (MBS) COUPLING

To 500 μl of $H_2O$ were added 5 mg of the peptide and the pH was adjusted to 8.5 with NaOH, to obtain a final concentration of 10 mg/ml. Citraconic anhydride was diluted in $H_2O$ to a concentration of 10 mg/ml. 500 μl of the anhydride solution were added to the peptide solution 100 μl at a time with adjustment of the pH to 8.5 between each addition. The solution was then stirred constantly at room temperature for 1 hour. This was followed by the addition of 100 μl of 1M sodium phosphate buffer (pH 7.2) and then 900 μl of 100 mM sodium phosphate buffer (pH 7.2). Sulfo-MBS was diluted in $H_2O$ to a concentration of 25 mg/ml and 400 μl of this solution were added to the peptide solution to obtain an MBS concentration of about 5 mg/ml. This solution was stirred constantly at room temperature for 30 minutes. 6 μl of β-mercaptoethanol were added for a final β-mercaptoethanol concentration of 35 mM. The solution was stirred constantly at room temperature for 1 hour. KLH was dissolved in PBS at 3 mg/ml and 2.5 ml were added to the peptide solution. The solution was stirred constantly at room temperature for 3 hours and then dialysed against 1 liter of PBS, with three changes of the PBS. The final peptide concentration was about 1 mg/ml and the final KLH concentration was about 1.5 mg/ml.

Antibody Generation

Rabbits were injected with the synthetic peptide solutions as follows. 250 μl each of the glutaraldehyde- and EDC-coupled peptide solutions were together mixed with 500 μl of Freund's adjuvant. This solution was injected intramuscularly into the rear legs of a rabbit, 500 μl per leg. The total amount of injected peptide was 0.5 mg. 500 μl of the synthetic peptide coupled to KLH with MBS were mixed with 500 μl of Freund's adjuvant. This solution was injected intramuscularly into the rear legs of another rabbit, 500 μl per leg. The total amount of injected peptide was 0.5 mg.

The synthetic peptide was loaded onto two lanes, 1.5 μg and 4 μg, of a gel (18% running, 5% stacking). The gel was blotted overnight at 30V and blocked with 3% milk in PBS. The gel was incubated overnight with rabbit serum diluted 1:250 in 1% milk/PBS followed by incubation with goat anti-rabbit-alkaline phosphatase diluted 1:1000 for 1 hour. The gel was then developed with substrate. The synthetic peptide was seen by comasie blue staining. The peptide was detected by the second bleed of each rabbit and was not detected by the preimmune serum of either rabbit.

Interaction between immobilized peptide and serum antibodies was further studied through surface plasmon resonance using BlAcore™. The synthetic peptide was covalently immobilized on a dextran matrix by amine coupling. Rabbit serum of different dilutions were injected over the surface for five minutes and the amount of antibody bound to the immobilized peptide determined. The titer is defined as the last dilution of the serum giving a positive response, that is, greater than 50 Resonance Units. Using this approach, antibodies were found to be present in serum from both rabbits and the interaction can be blocked by preincubating the serum with the peptide. Antibodies in serum of the rabbits were found not to interact with an immobilized unrelated peptide.

Experiments Involving Rats and Antibodies to the Chemically Synthesized Peptide

Antibody serum was prepared in 10 mM Tris.Cl at pH 7.4. Each of five rats received 100 μl of the solution by injection into the left gluteus maximus. Each rat of a second group of five rats was treated similarly, but with an additional injection of solution containing 45 μg of the polypeptide (SEQ ID NO:1) into the right gluteus maximus. Each rat of a third group of five rats received an injection of 100 μl of 10 mM Tris.Cl at pH 7.0.

Each of the fifteen rats was then injected as before with tetracycline hydrochloride, in the amount of 24 mg per Kg of body weight. A second dose of tetracycline hydrochloride was injected about 48 hours later. The rats were sacrificed after about another 24 hours.

Figure 5:
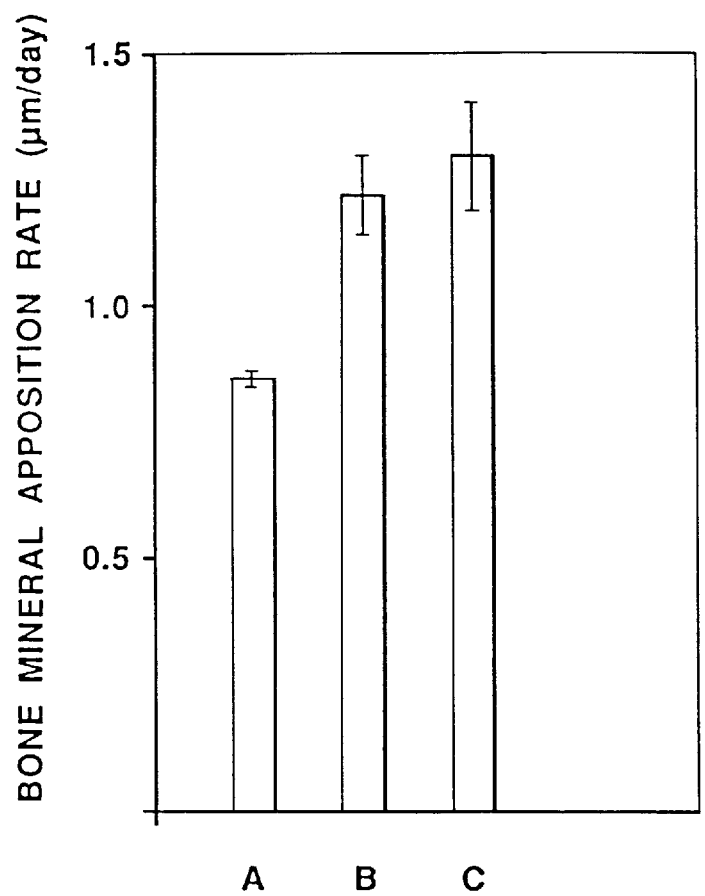
FIG. 5 graphically depicts the bone mineral apposition rate of intact rats as determined by tetracycline labelling. Group A rats were treated with rabbit antibodies to the chemically synthesized normal polypeptide (SEQ ID NO:1). Group B rats were treated with the same antibodies and the polypeptide itself. Group C is the control group. The error bars indicate ±1 standard deviation (S.D.).

The bone mineral apposition rate was determined by measurements, described above, of the lower right femoral metaphysis. The results are given in Table Five and FIG. 5.

TABLE FIVE

Bone Mineral Apposition Rates in Rats Injected with
Antibody to the Chemically Synthesized Peptide

|  | Group A | Group B | Group C |
|---|---|---|---|
| Mean (μm/day) | 0.86 | 1.22 | 1.30 |
| S.D. | 0.02 | 0.08 | 0.11 |
| N | 5 | 5 | 5 |

|  | t | d.f | p |
|---|---|---|---|
| Group A vs Group B | 8.06 | 8 | >0.2 |
| Group A vs Group C | 7.57 | 8 | <0.001 |
| Group B vs Group C | 1.24 | 8 | >0.2 |

Methodology and products can be thus be developed using antibody to the polypeptide for use in detecting the polypeptide with which the antibody binds. For example, antibody can be linked to or conjugated with any of several well known reporter systems set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluorescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such a method based on antigenic response to the chemically synthesized human polypeptide (SEQ ID NO:1) could be developed and variants of the polypeptide obtained, as described above for amino acid substitution, deletion and addition, (and conjugates) could then be pre-screened as potential bone stimulating factors. Those that react positively with the antibody to the already known peptide could then be tested for bone stimulatory effects in vivo using the system described herein for rats, for example.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

Experiments Involving Chemically Synthesized Human Polypeptide Containing Cysteine→Alanine Substitution A modified sequence (SEQ ID NO:3) of the chemically synthesized peptide (SEQ ID NO:1) obtained by substitution of the cysteine residue at position 13 by alanine was prepared by standard chemical procedures. An alanine residue is sterically similar to a reduced cysteine residue while rendering the polypeptide incapable of spontaneous dimerization. A tricine SDS electrophoretic gel of the modified and unmodified (normal) peptides is shown in FIG. 6.

Experiments were carried out on three groups of six rats weighing between 295 and 320 g. A 1 mg per ml solution of the modified peptide (SEQ ID NO:3) was prepared in 0.1% acetic acid. A 1 mg per ml solution of the normal peptide (SEQ ID NO:1) was prepared in 0.1% acetic acid. Each rat of a first of the groups had subcutaneously injected into its right thigh 0.1 ml of the modified peptide solution. Similarly, each rat of the second group was injected with 0.1 ml of the normal peptide solution. Each rat of the third group, the control group, was injected with 0.1 ml of 0.1% acetic acid solution. Immediately following these injections, each rat was injected intramuscularly with 24 mg per Kg body weight of tetracycline hydrochloride dissolved in 0.5 ml of water. A second dose of tetracycline hydrochloride was administered 48 hours later. The animals were sacrificed 24 hours after the second dose by $CO_2$ narcosis. The lower metaphysis of the right femur was dissected out and fixed in a 10% aqueous solution of formaldehyde buffered at pH 7.2 by acetate buffer. Bone sections were prepared for measurement as described above.

Figure 7:
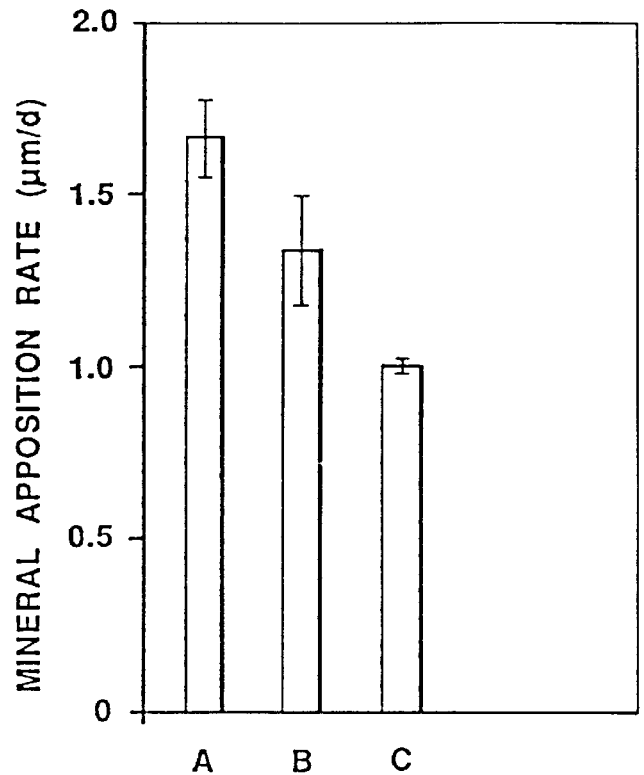
FIG. 7 graphically depicts the bone mineral apposition rate ($\mu$m per day) in rats injected with the chemically synthesized human polypeptide (SEQ ID NO:1), Group A; the modified chemically synthesized human polypeptide (SEQ ID NO:3), Group B; and control, Group C. (N=6 for all groups). The error bars indicate ±1 standard deviation (S.D.).

The results are tabulated in Table Six and graphically depicted in FIG. 7. As can be seen, the bone apposition rate for rats injected with the modified polypeptide is significantly greater than that for those of the control group but below the bone apposition rate shown for the rats injected with the normal peptide.

TABLE SIX

Comparison of the Group Arithmetic Means Among Groups Injected with Modified Peptide, Unmodified Peptide and Control

|  | Group A | Group B | Control Group |
|---|---|---|---|
| Mean | 1.67 μm/d | 1.35 μm/d | 1.02 μm/d |
| S.D. | 0.11 μm/d | 0.16 μm/d | 0.010 μm/d |
| N | 6 | 6 | 6 |

|  | t | d.f | p |
|---|---|---|---|
| Group A vs Control (Group C) | 12.2 | 10 | <0.001 |
| Group B vs Control (Group C) | 4.69 | 10 | <0.001 |
| Group A vs Group B | 3.97 | 10 | <0.005 |

Experiments Involving N-Terminus Fragments of the 36-Amino Acid Human Polypeptide Polypeptides having the amino acid sequences identified as SEQ ID NOs:4, 5, 6 and 7 were synthesized according to well known chemical procedures.

Sprague-Dawley rats were used as test animals to determine bone mineral apposition rate, as described above. Male rats having weights between 300 and 380 g were subject to subcutaneous injection after one week of acclimatization. Each animal was injected with 200 μl of a 0.1% acetic acid test solution, solutions having been prepared to obtain a dosage of about 25 nmol of polypeptide per animal. Each test dose was immediately followed by intramuscular injection of 24 mg per Kg of body weight of tetracycline hydrochloride. A second injection of tetracycline was made 48 hours later.

Figure 8:
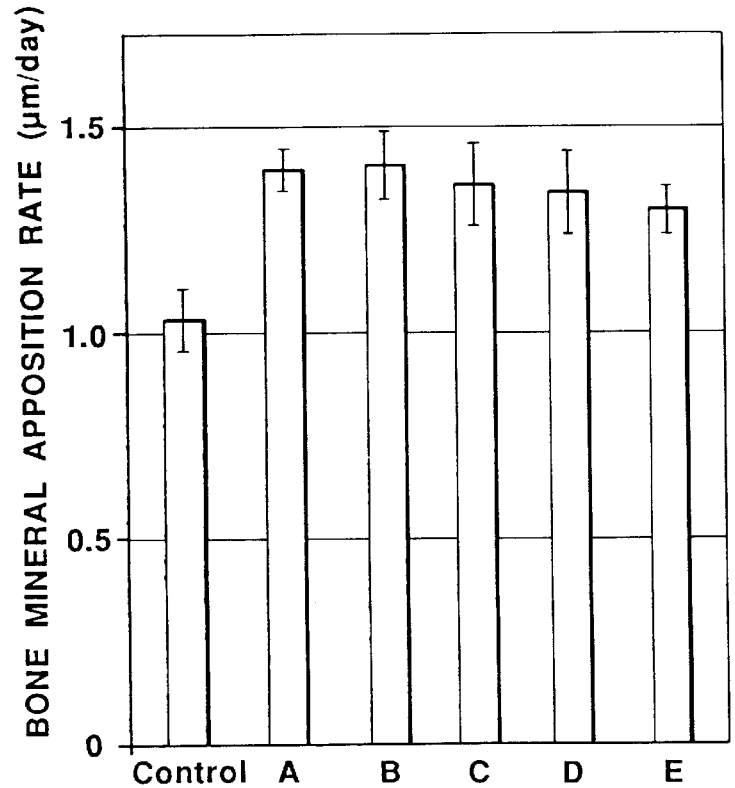
FIG. 8 graphically depicts the bone mineral apposition rate ($\mu$m per day) in rats injected with N-terminus chemically synthesized polypeptides: SEQ ID NO:1 (Group A); SEQ ID NO:7 (Group B); SEQ ID NO:6 (Group C); SEQ ID NO:5 (Group D); and SEQ ID NO:4 (Group E). (N=6 for all groups). The error bars indicate ±1 standard deviation (S.D.).

Control Group: 0.1% acetic acid solution
Group A: SEQ ID NO:1:
Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro
Group E: SEQ ID NO:4:
Gly Ile Gly Lys Arg Thr Asn Glu His Thr Ala Asp Cys Lys Ile Lys Pro Asn Thr Leu His Lys Lys Ala Ala Glu Thr Leu Met Val
Group D: SEQ ID NO:5:
Gly Ile Gly Lys Arg Thr Asn Glu His Thr Ala Asp Cys Lys Ile Lys Pro Asn Thr Leu His Lys Lys Ala Ala
Group C: SEQ ID NO:6:
Gly Ile Gly Lys Arg Thr Asn Glu His Thr Ala Asp Cys Lys Ile Lys Pro Asn Thr Leu
Group B: SEQ ID NO:7:
Gly Ile Gly Lys Arg Thr Asn Glu His Thr Ala Asp Cys Lys Ile Bone mineral apposition rates were determined by measurements of the lower metaphysis of the right femur, as described previously. Results obtained are summarized in Table Seven and graphically depicted in FIG. 8. As can be seen, all of the polypeptides tested had a positive effect on bone apposition rate.

TABLE SEVEN

Comparison of the Group Arithmetic Means Among Groups Injected with N-terminus Variants

|  | Group A | Group B | Group C | Group D | Group E | Control |
|---|---|---|---|---|---|---|
| Mean | 1.40 | 1.41 | 1.37 | 1.35 | 1.31 | 1.03 |
| S.D. | 0.05 | 0.08 | 0.09 | 0.10 | 0.06 | 0.06 |
| N | 6 | 6 | 6 | 6 | 6 | 6 |

|  | t | d.f. | p |
|---|---|---|---|
| Group A vs Control | 5.18 | 10 | <0.001 |
| Group B vs Control | 9.67 | 10 | <0.001 |
| Group C vs Control | 7.64 | 10 | <0.001 |
| Group D vs Control | 6.92 | 10 | <0.001 |
| Group E vs Control | 7.99 | 10 | <0.001 |
| Group A vs Group B | 0.14 | 10 | >0.5 |
| Group A vs Group C | 0.40 | 10 | >0.5 |
| Group A vs Group D | 0.66 | 10 | >0.5 |
| Group A vs Group E | 1.30 | 10 | >0.2 |
| Qroup B vs Group C | 0.82 | 10 | >0.4 |
| Group B vs Group D | 1.19 | 10 | >0.2 |
| Group B vs Group E | 2.49 | 10 | <0.05 |

Figure 9:
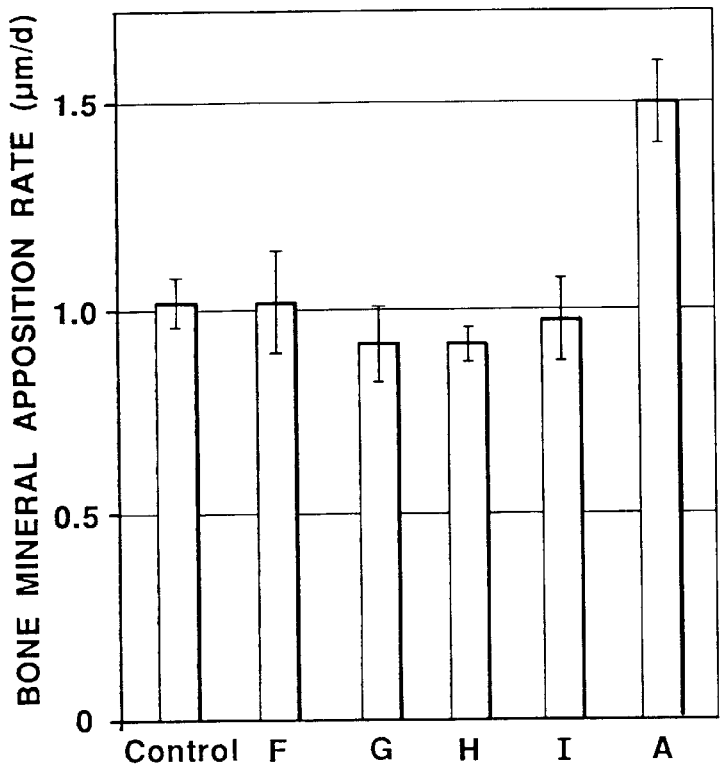
FIG. 9 graphically depicts the bone mineral apposition rate ($\mu$m per day) in rats injected with non-N-terminus chemically synthesized polypeptide fragments SEQ ID NO:1 (Group A); SEQ ID NO:14 (Group F); SEQ ID NO:13 (Group G); SEQ ID NO:12 (Group H); and SEQ ID NOs:8, 9,10 & 11 (Group I). (N=6 for all groups). The error bars indicate ±1 standard deviation (S.D.).

Experiments Involving Non-N-Terminus Fragments of the 36-Amino Acid Human Polypeptide Polypeptide fragments of the normal polypeptide (SEQ ID NO:1) were also synthesized and tested for bone stimulatory activity as with the C-terminus fragments.
Control Group: 0.1% acetic acid
Group A: SEQ ID NO:1:
Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro
Group F: SEQ ID NO:14:
Group G: SEQ ID NO:13:
Group H: SEQ ID NO:12:
Group I: SEQ ID NOs:8, 9, 10 & 11 (mixture):
Leu His Lys Lys Ala Ala Glu Thr Leu Met Val Leu Asp Gln Asn Gln
Leu His Lys Lys Ala Ala Glu Thr Leu Met Val Leu Asp Gln Asn
Leu His Lys Lys Ala Ala Glu Thr Leu Met Val Leu Asp Gln
Leu His Lys Lys Ala Ala Glu Thr Leu Met Val Leu Asp Bone mineral apposition rates were again deteremined by measuresment of the lower metaphysis of the right femur. Results obtained are summarized in Table Eight and graphically depicted in FIG. 9. As can be seen in FIG. 9, none of the Non-N-terminus variants increased the bone apposition rate with respecct to the control.

TABLE EIGHT

Summary of the Group Arithmetic Means for Bone Apposition Rates of Rats Injected with Non-N-terminus Variants

|  | Group A | Group F | Group G | Group H | Group I | Control |
|---|---|---|---|---|---|---|
| Mean($\mu$m/day) | 1.50 | 1.02 | 0.92 | 0.92 | 0.98 | 1.02 |
| S.D. | 0.09 | 0.12 | 0.09 | 0.04 | 0.09 | 0.06 |
| N | 6 | 6 | 6 | 6 | 6 | 6 |

Nucleic acid (DNA) sequences coding for the portions of the normal polypeptide would be as follows:
SEQ ID NO:15 (corresponding to SEQ ID NO:4):
GGG ATC GGA AAA CGA ACA AAT GAA CAT ACG GCA GAT TGT AAA ATT AAA CCG AAC ACC TTG CAT AAA AAA GCT GCA GAG ACT TTA ATG GTC
SEQ ID NO:16 (corresponding to SEQ ID NO:5):
GGG ATC GGA AAA CGA ACA AAT GAA CAT ACG GCA GAT TGT AAA ATT AAA CCG AAC ACC TTG CAT AAA AAA GCT GCA
SEQ ID NO:17 (corresponding to SEQ ID NO:6):
GGG ATC GGA AAA CGA ACA AAT GAA CAT ACG GCA GAT TGT AAA ATT AAA CCG AAC ACC TTG
SEQ ID NO:18 (corresponding to SEQ ID NO:7):
GGG ATC GGA AAA CGA ACA AAT GAA CAT ACG GCA GAT TGT AAA ATT Accordingly, a vector incorporating such a DNA sequence could be constructed for use in synthesizing a polypeptide, as described previously, an particularly in international patent application No. PCT/CA 94/00144.

It will of course be understood, that antibodies to any of the polypeptides disclosed herein could be generated, as described in connection with the normal polypeptide (SEQ ID NO:1).

It will also be understood, without the intention of being limited thereby, that a variety of substitutions of amino acids is possible while "preserving" the three-dimensional structure responsible for the bone stimulatory effect of the polypeptides disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, cysteine, asparagine and glutamine could possibly be made. This being said, the linkage of the peptides together by the disulfide bridge appears to be of some importance, and so the lone cysteine residue should probably be held intact and other amino acids capable of forming a disulfide linkage not be substituted elsewhere in the sequence. Substitutions among the charged acidic amino acids, aspartic acid and glutamic acid, could probably be made, as could substitutions among the charged basic amino acids, lysine and arginine. Substitutions among the aromatic amino acids, including phenyalanine, histidine, tryptophan and tyrosine would also likely be possible. These sorts of substitutions and interchanges are well known to those skilled in the art. Other substitutions might well be possible.

The polypeptide identified as SEQ ID NO:7 contains 15 amino acids while the polypeptide identified as SEQ ID NO:1 has 36 amino acids, the former thus having 42% of the sequence of the latter. It is thus thought thought that a polypeptide having an amino acid sequence with about 40% homology or more with the sequence identified as SEQ ID NO:1 (or SEQ ID NO:3) may well retain part or all of the bone stimulating activity of the sequence.

The importance of the N-terminus portion of the sequence is evident from the results described herein. The polypeptide having the first 15 N-terminus amino acids (SEQ ID NO:7) of the normal polypeptide (SEQ ID NO:1) displays bone stimulatory activity while polypeptides lacking the first four N-terminus amino acids, but having amino acids 5 to 15 (SEQ ID NO:14) or amino acids 5 to 34 (SEQ ID NO:13) do not display bone stimulatory activity. It may be that it is possible to delete more amino acids from the C-terminus end of the polypeptide identified as SEQ ID NO:7.

As with the normal peptide (SEQ ID NO:1), an active subsequence containing a cysteine residue (i.e., SEQ ID Nos:4, 5, 6 and 7) is likely to spontaneously dimerize and exist in the dimeric form.

In the context of this invention, a peptide containing an amino acid sequence that can be aligned with that of SEQ ID NO:1 such that at least about 30% of individual amino acid residues of the original sequence are conserved, allowing for a limited number of insertions or deletions between aligned sequences, and being cognizant of the importance of the N-terminus portion of the normal polypeptide might well retain bone stimulatory activity. Of course, it would also be expected that the greater percentage of homology, say 40%, 50%, 60%, 70%, 80%, 90%, or more, could increase the degree of retained bone stimulating activity.

Insofar as deletion of one or more amino acids is concerned, it has now been shown that deletions of a number of amino acids from the C-terminus end of the sequence (SEQ ID NO:1) are possible. It may be possible to delete a smaller number from the C-terminus end also while retaining the three-dimensional configuration of the subsequence of the polypeptide responsible for bone stimulatory activity. Internal deletions, although likely to be possible to some limited extent, should be few, and should probably amount to no more than about five amino acids, especially with respect to the first fifteen or so C-terminus amino acids of the normal polypeptide.

Additions of amino acids could very likely be made at the ends of the sequence and symmetrical or nearly symmetrical additions to the carboxy and amino terminals are likely to be possible. Internal additions, although likely to be possible to some limited extent, should be few, and should probably amount to no more than about five amino acids, and preferably fewer.

Of the above-listed modifications to the sequence, terminal additions, deletions or substitutions are most likely to be most useful, as such a modification can serve a variety of functions: an identifying group as for use in a radioimmunoassay; or a linking group, as examples.

A further advantage may be obtained through chimeric forms of the protein, as known in the art. A DNA sequence encoding the entire protein, or a portion of the protein, could thus be linked with a sequence coding for the C-terminal portion of $E.$ $coli$ $\beta$-galactosidase to produce a fusion protein, for example. An expression system for human respiratory syncytial virus glycoproteins F and G is described in U.S. Pat. No. 5,288,630, issued Feb. 22, 1994, and references cited therein, for example.

What is claimed is:

1. An isolated polypeptide comprising the amino acid sequence identified as SEQ ID NO:4.

2. An isolated polypeptide comprising the amino acid sequence identified as SEQ ID NO:5.

3. An isolated polypeptide comprising the amino acid sequence identified as SEQ ID NO:6.

4. An isolated polypeptide comprising the amino acid sequence identified as SEQ ID NO:7.

5. A dimeric polypeptide where each monomer of polypeptide contains the amino acid sequence set forth in claim 1, wherein the monomers are linked to each other by a disulfide bridge between the cysteine residues of the respective sequences.

6. A dimeric polypeptide where each monomer of polypeptide contains the amino acid sequence set forth in claim 2, wherein the monomers are linked to each other by a disulfide bridge between the cysteine residues of the respective sequences.

7. A dimeric polypeptide where each monomer of polypeptide contains the amino acid sequence set forth in claim 3, wherein the monomers are linked to each other by a disulfide bridge between the cysteine residues of the respective sequences.

8. A dimeric polypeptide where each monomer of polypeptide contains the amino acid sequence set forth in claim 4, wherein the monomers are linked to each other by a disulfide bridge between the cysteine residues of the respective sequences.

9. An isolated polypeptide exhibiting bone growth stimulatory activity in mammals, the polypeptide comprising a monomer comprising the amino acid sequence set forth in claim 1, and diners thereof; wherein the monomers are linked to each other by a disulfide bridge between the cysteine residues of the respective sequences.

10. An isolated polypeptide exhibiting bone growth stimulatory activity in mammals, the polypeptide comprising a monomer comprising the amino acid sequence set forth in claim 2, and dimers thereof; wherein the monomers are linked to each other by a disulfide bridge between the cysteine residues of the respective sequences.

11. An isolated polypeptide exhibiting bone growth stimulatory activity in mammals, the polypeptide comprising a monomer comprising the amino acid sequence set forth in claim 3, and dimers thereof; wherein the monomers are linked to each other by a disulfide bridge between the cysteine residues of the respective sequences.

12. An isolated polypeptide exhibiting bone growth stimulatory activity in mammals, the polypeptide comprising a monomer comprising the amino acid sequence set forth in claim 4, and dimers thereof; wherein the monomers are linked to each other by a disulfide bridge between the cysteine residues of the respective sequences.

13. A method of increasing bone growth in a mammal by administering a therapeutically effective amount of a polypeptide of claim 1.

14. A method of increasing bone growth in a mammal by administering a therapeutically effective amount of a polypeptide of claim 2.

15. A method of increasing bone growth in a mammal by administering a therapeutically effective amount of a polypeptide of claim 3.

16. A method of increasing bone growth in a mammal by administering a therapeutically effective amount of a polypeptide of claim 4.

17. A method of increasing bone growth in a mammal by administering a therapeutically effective amount of a polypeptide of claim 5.

18. A method of increasing bone growth in a mammal by administering a therapeutically effective amount of a polypeptide of claim 6.

19. A method of increasing bone growth in a mammal by administering a therapeutically effective amount of a polypeptide of claim 7.

20. A method of increasing bone growth in a mammal by administering a therapeutically effective amount of a polypeptide of claim 8.

21. A method of increasing bone growth in a mammal by administering a therapeutically effective amount of a polypeptide of claim 9.

22. A method of increasing bone growth in a mammal by administering a therapeutically effective amount of a polypeptide of claim 10.

23. A method of increasing bone growth in a mammal by administering a therapeutically effective amount of a polypeptide of claim 11.

24. A method of increasing bone growth in a mammal by administering a therapeutically effective amount of a polypeptide of claim 12.

25. A polypeptide exhibiting bone growth stimulatory activity in mammals comprising a sequence of amino acids which is encoded by a DNA that specifically hybridizes with DNA encoding the polypeptide set forth in claim 1.

26. A polypeptide exhibiting bone growth stimulatory activity in mammals comprising a sequence of amino acids which is encoded by a DNA that specifically hybridizes with DNA encoding the polypeptide set forth in claim 2.

27. A polypeptide exhibiting bone growth stimulatory activity in mammals comprising a sequence of amino acids which is encoded by a DNA that specifically hybridizes with DNA encoding the polypeptide set forth in claim 3.

28. A ploypeptide exhibiting bone growth stimulatory activity in mammals comprising a sequence of amino acids which is encoded by a DNA that specifically hybridizes with DNA encoding the polypepetide set forth in claim 4.

29. A chimeric bone growth stimulating factor comprising the polypeptide set forth in claim 1 linked to another polypeptide.

30. A chimeric bone growth stimulating factor comprising the polypeptide set forth in claim 2 linked to another polypeptide.

31. A chimeric bone growth stimulating factor comprising the polypeptide set forth in claim 3 linked to another polypeptide.

32. A chimeric bone growth stimulating factor comprising the polypeptide set forth in claim 4 linked to another polypeptide.

33. A method of increasing bone growth in a mammal by administering a therapeutically effective amount of the protein of claim 25.

34. A method of increasing bone growth in a mammal by administering a therapeutically effective amount of the protein of claim 26.

35. A method of increasing bone growth in a mammal by administering a therapeutically effective amount of the protein of claim 27.

36. A method of increasing bone growth in a mammal by administering a therapeutically effective amount of the protein of claim 28.

37. A method of increasing bone growth in a mammal by administering a therapeutically effective amount of the chimeric bone growth stimulating factor of claim 29.

38. A method of increasing bone growth in a mammal by administering a therapeutically effective amount of the chimeric bone growth stimulating factor of claim 30.

39. A method of increasing bone growth in a mammal by administering a therapeutically effective amount of the chimeric bone growth stimulating factor of claim 31.

40. A method of increasing bone growth in a mammal by administering a therapeutically effective amount of the bone growth stimulating factor of claim 32.

* * * * *